US012622800B2

(12) United States Patent
Kim et al.

(10) Patent No.: US 12,622,800 B2
(45) Date of Patent: May 12, 2026

(54) ASSISTIVE WEARABLE SYSTEM FOR RELIEVING MUSCLE FATIGUE IN THE NECK AND SHOULDERS

(71) Applicants: KOREA INSTITUTE OF SCIENCE AND TECHNOLOGY, Seoul (KR); SEOUL NATIONAL UNIVERSITY R&DB FOUNDATION, Seoul (KR)

(72) Inventors: Seung-Won Kim, Seoul (KR); Hang Man Cho, Seoul (KR); Jung-Hwan Moon, Seoul (KR); Jae-Ryeong Choi, Seoul (KR); Kyu-Jin Cho, Seoul (KR)

(73) Assignees: KOREA INSTITUTE OF SCIENCE AND TECHNOLOGY, Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 165 days.

(21) Appl. No.: 18/432,792

(22) Filed: Feb. 5, 2024

(65) Prior Publication Data

US 2025/0152396 A1 May 15, 2025

(30) Foreign Application Priority Data

Nov. 14, 2023 (KR) ........................ 10-2023-0156983

(51) Int. Cl.
*A61F 5/37* (2006.01)
*A61F 5/01* (2006.01)
*A61H 1/02* (2006.01)
(52) U.S. Cl.
CPC .............. *A61F 5/3707* (2013.01); *A61F 5/01* (2013.01); *A61H 1/0218* (2013.01); *A61H 1/0296* (2013.01)

(58) Field of Classification Search
CPC ...... A61F 5/026; A61F 5/055; A61F 5/05883; A61F 5/3707; A42B 3/0473; A61H 1/008;
(Continued)

(56) References Cited

U.S. PATENT DOCUMENTS 3,359,976 A * 12/1967 Laval, Jr. ................ A61F 5/055
602/17
5,319,997 A * 6/1994 Galloway ................ B66D 3/04
74/505
(Continued)

FOREIGN PATENT DOCUMENTS

JP     2020-146760 A    9/2020
KR      10-2174370 B1   11/2020
KR   10-2023-0000723 A    1/2023

OTHER PUBLICATIONS

Korean Office Action Issued on Jun. 19, 2025, in Counterpart Korean Patent Application No. 10-2023-0156983 (6 Pages in English, 6 Pages in Korean).

*Primary Examiner* — Rachael E Bredefeld
*Assistant Examiner* — Seth R. Brown
(74) *Attorney, Agent, or Firm* — NSIP Law

(57) ABSTRACT

The present disclosure relates to relates to a assistive wearable system for relieving muscle fatigue in the neck and shoulders, the assistive wearable system includes a head gear mounted to cover a head of a user, a wearable platform mounted on an upper body of the user, and a wire tension controller that maintains tension of a wire by being seated on the wearable platform and fixing to operate a semi-active ratchet mechanism structure as a brake to detect a moment a movement of the wire stops as connected to the head gear by the wire, and stop unwinding of the wire, wherein the ratchet mechanism rotates the ratchet based on the unwinding and pulling of the wire.

7 Claims, 5 Drawing Sheets

(58) Field of Classification Search
CPC .. A61H 1/0218; A61H 1/0292; A61H 1/0296;
A61H 2201/0157; A61H 2201/1604;
A61H 2201/1607; A61H 2201/1609;
A61H 2201/1611; A61H 2201/1614;
A61H 2201/1616; A61H 2201/165; A61H
2201/1652; A61H 2205/02; A61H
2205/04; A63B 23/025; A63B 21/00065;
A63B 21/00069; A63B 21/4003; A63B
21/4005; A63B 21/4025; A63B 71/10;
A61B 2090/502; A61B 90/53; A61B
90/60
USPC ...... 602/17–19, 32, 36; 482/10, 120; 74/575
See application file for complete search history.

(56) References Cited

U.S. PATENT DOCUMENTS

| | | | | |
|---|---|---|---|---|
| 5,451,202 | A * | 9/1995 | Miller ................. | A61H 1/0218 |
| | | | | 606/241 |
| 12,048,598 | B1 * | 7/2024 | Johnson ................ | A61B 90/60 |
| 2013/0261520 | A1 * | 10/2013 | Grenander ............. | A61F 5/058 |
| | | | | 602/18 |
| 2014/0081180 | A1 * | 3/2014 | Ghajar ................... | A61F 5/055 |
| | | | | 600/595 |
| 2017/0245576 | A1 * | 8/2017 | Hetzler ............... | A42B 3/0473 |
| 2022/0257336 | A1 * | 8/2022 | Malcolm ................. | A61F 5/02 |

* cited by examiner

ASSISTIVE WEARABLE SYSTEM FOR RELIEVING MUSCLE FATIGUE IN THE NECK AND SHOULDERS

CROSS-REFERENCE TO RELATED APPLICATION

The present application claims the benefit under 35 USC 119(a) of Korean Application No. 10-2023-0156983 filed on Nov. 14, 2023, in the Korean Intellectual Property Office, the entire disclosure of which is incorporated herein by reference for all purposes.

BACKGROUND OF THE INVENTION

Field of the Invention

The present disclosure relates to an assistive wearable system for relieving muscle fatigue in the neck and shoulders, and more specifically, to an assistive wearable system driven by a ratchet mechanism that operates with simple movements of the user.

Description of the Related Art

People who maintain a certain posture for a long time or work in a bent posture may cause neck pain, dizziness, etc. These discomforts can contribute to musculoskeletal issues such as a turtle neck or cervical disc problems, leading to pain in the shoulder or trapezius muscle due to the stiffening of the cervical spine. However, there are therapeutic braces available on the market to alleviate pain resulting from these symptoms, such as pneumatic braces that lift the neck, massagers, braces for patients with cervical disc herniation, and correctors, etc. Nevertheless, these devices must be worn only during the treatment period and cannot be used in daily life.

In addition, wearable systems designed to alleviate user muscle fatigue or wearable aids that enable users to perform computer work and daily activities freely in a bent position while wearing them are not widely available. In other words, to achieve an assistive wearable system that can be worn during work to prevent neck and shoulder pain, there is a need for a wearable system that distributes the weight of muscle fatigue during maintenance. This enables the wearer to move comfortably and freely at work, thereby maintaining a specific posture without the assistive wearable system becoming an obstacle.

SUMMARY OF THE INVENTION

The embodiments of the present specification aim to address the technical challenge of minimizing the continuous energy consumption of the motor embedded in a wearable system that operates in place of the muscles used to maintain the user's lowered head posture. This is done to enable continuous and long-term operation of the device. The objective is also to equip the device with a mechanism that detects the user's movements, allowing the user to easily fix their head at the desired angle without using limbs.

A configuration of an assistive wearable system for relieving muscle fatigue in the neck and shoulders, as disclosed herein to achieve the above purpose, comprises a head gear mounted to cover a user's head; a wearable platform mounted on an upper body of the user; and a wire tension controller that maintains the tension of a wire. The wire tension controller is seated on the wearable platform and is fixed to operate a semi-active ratchet mechanism structure as a brake. This detects the moment when the movement of the wire, connected to the headgear by the wire, stops and prevents unwinding of the wire. The ratchet mechanism rotates the ratchet based on the unwinding and pulling of the wire.

In addition, the wearable platform may include a wire sheath formed to be located at the rear of the wearable platform and spaced apart from the wire tension controller. This prevents rotational torque caused by twisting or lifting left and right according to the movement of the user and maintains the tension of the wire.

Furthermore, the wearable platform may further include a wire separator that divides and connects the wire to both sides of the headgear; and a neck brace joined to the wire separator through a protruding joint. The neck brace is attached to the upper part of the wearable platform to support the wire separator and the wire behind the user's neck and is coupled to the upper body of the user.

In addition, the wire tension controller, connected to the headgear by the wire, may include an incremental encoder that detects the amount of rotation of a wire winding frame in the wire tension controller according to the movement of the wire; a pawl for fixing a ratchet in the wire tension controller and the rotation of the ratchet to maintain the tension of the wire; a ball plunger for holding the pawl in different locations according to the fixation and release of the pawl based on rotation of the ratchet; and a power unit that operates the pawl based on an electrical signal from the incremental encoder based on the movement of the wire.

In addition, the incremental encoder may generate the electrical signal that operates to cause the pawl to fix the rotation of the ratchet when the amount of rotation of the wire winding frame connected to the wire is not detected due to no movement of the wire for a predetermined period of time.

In addition, the pawl may prevent rotation of the ratchet by engaging the ratchet to stop unwinding of the wire due to rotation of the ratchet.

In addition, the power unit may detect the electrical signal generated from the incremental encoder and provide power to operate the pawl.

Furthermore, the head gear, connected to the wire tension controller by the wire, may further include an inertial measurement unit (IMU) sensor capable of measuring a head angle information of the user using tilt inertia according to the head angle of the user.

According to the above-described embodiments of the present disclosure, it is possible to relieve muscle fatigue of the splenius capitis and trapezius muscles by proposing a assistive wearable system that can maintain the user's head-down posture, and it is possible to provide a robust device with minimal power consumption by assisting the user at the user's desired head angle by minimizing the power consumption of the wearable system to maintain the bowed posture.

DETAILED DESCRIPTION OF THE EMBODIMENTS

Hereinafter, embodiments of the present disclosure will be described in detail with reference to the drawings. However, detailed descriptions of known functions or configurations that may obscure the gist of the embodiments are omitted in the following description and attached drawings. In addition, throughout the specification, 'including' a certain component does not mean excluding other components unless specifically stated to the contrary, but rather means that other components may be further included.

The terms used in the present disclosure are only used to describe specific embodiments and are not intended to limit the present disclosure. Singular expressions include plural expressions unless the context clearly indicates otherwise. In the present disclosure, terms such as "comprise" or "include" are intended to designate the presence of described features, numbers, steps, operations, components, parts, or combinations thereof, but should be understood that this does not exclude in advance the possibility of the presence or addition of one or more other features, numbers, steps, operations, components, parts, or combinations thereof.

Unless specifically defined otherwise, all terms used herein, including technical or scientific terms, have the same meaning as generally understood by a person of ordinary skill in the technical field to which the present disclosure pertains. Terms defined in commonly used dictionaries should be interpreted as having a meaning consistent with the meaning in the context of the related technology, and unless clearly defined in the present disclosure, should not be interpreted as having an ideal or excessively formal meaning.

Figure 1A:
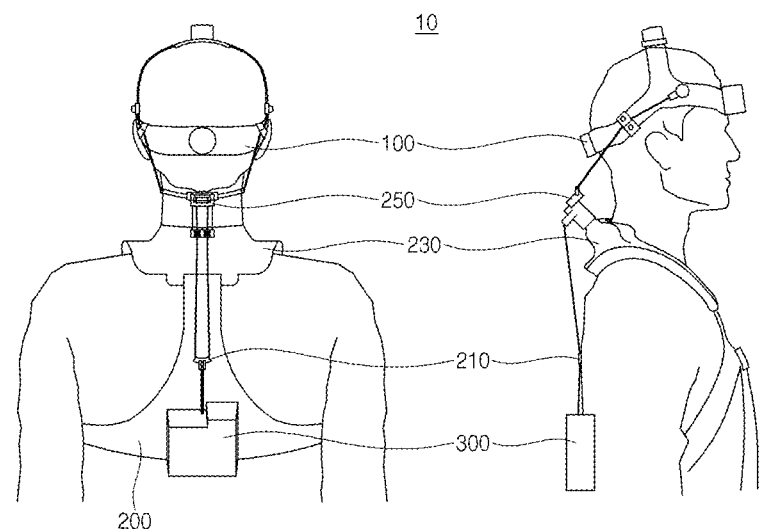
FIGS. 1A to 1C are diagrams illustrating a assistive wearable system for relieving muscle fatigue of the neck and shoulders according to an embodiment of the present disclosure.
Figure 1B:
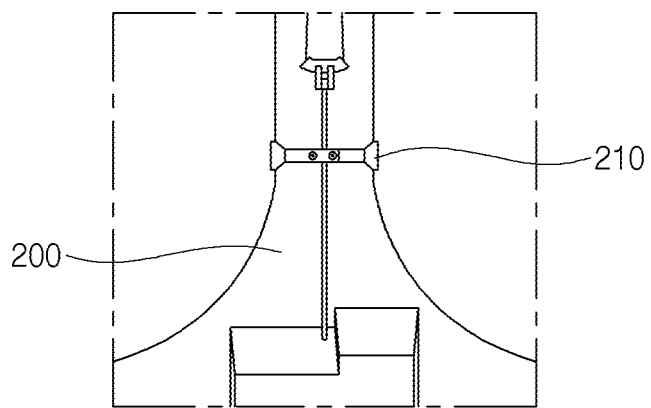
Figure 1C:
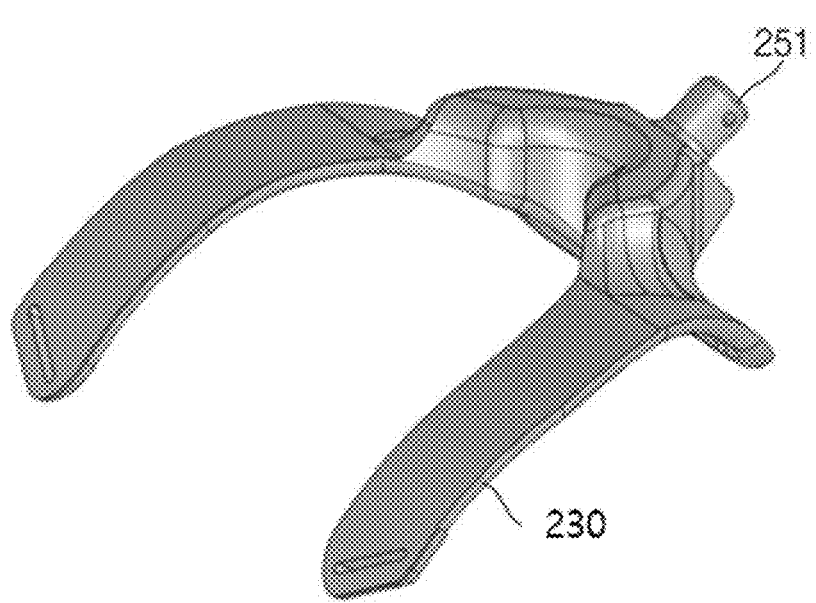

FIGS. 1A to 1C are diagrams illustrating a assistive wearable system 10 for relieving muscle fatigue of the neck and shoulders according to an embodiment of the present disclosure.

Referring to FIG. 1A, the assistive wearable system 10 of this embodiment may include a headgear 100, a wearable platform 200, a wire sheath 210, a neck brace 230, a wire separator 250, and a wire tension controller 300.

The headgear 100 may be mounted to cover a head of a user using the assistive wearable system. At this time, the head gear 100 may be connected to the wire tension controller 300 by a wire from the side rather than the rear of the head gear 100. Through this, when the assistive wearable system 10 operates, when tension of the wire occurs, it is possible to prevent a phenomenon in which weight is added to the back of the user's head and the headgear 100 tries to come off the user's head, and to stably support or pull the head. Additionally, it is possible to prevent the user's neck from being burdened by the weight of the user's head being applied to the rear.

The head gear 100 may be equipped with an inertial measurement unit (IMU) sensor capable of measuring the user's head angle information using the tilt inertia according to the head angle of the user using the assistive wearable system 10. The IMU sensor can monitor the user's head tilt angle through an observation apparatus separately provided in the assistive wearable system 10. That is, the assistive wearable system 10 can measure the angle of the user's head and the acceleration and angular velocity of the user's head movement acquired through the IMU sensor in real time. Through this, the user's posture and the operating range of the wire can be measured, which is expected to help correct posture in a customized way.

The wearable platform 200 may be mounted on an upper body of the user. At this time, the shape of the wearable platform 200 may be a vest, but the shape may vary depending on the user's convenience and work environment.

Referring to FIG. 1B, the wire sheath 210 may be formed to be located at the rear of the wearable platform 200 and spaced higher than the wire tension controller 300. The wire sheath 210 is formed to be spaced apart from the wire tension controller 300, thereby maintaining the tension of the wire connected between the head gear 100 and the wire tension controller 300. When tension is generated at the other end of the wire while the wire tension controller 300 is fixed to the wearable platform 200, as a pulling force is applied to the wire tension controller 300, a rotational force (torque) is generated in the outward (normal) direction of the user's back and the length of the wire changes as the position of the wire tension controller moves, so a phenomenon in which the tension of the wire is lost occurs. Additionally, the wearable platform 200 may be twisted or lifted left and right according to the user's movement, thereby generating a rotational force. In order to solve this problem, by forming the wire sheath 210 in the assistive wearable system 10, the pulling force of the wire is applied to the wire sheath 210 rather than to the wire tension controller 300, so that displacement of the wearable platform 200 is minimized and tension of the wire can be maintained. In addition, as the wearable platform 200 worn by the user is bound to the user's body, the lifting phenomenon can be prevented by preventing the clearance between the user and the assistive wearable system 10, and the wire can be supported to maintain the tension of the wire.

Referring to FIG. 1C, the wearable platform 200 may have the neck brace 230 formed on the top of the wearable platform 200 so that it can be coupled to the upper body of the user, and the wire separator 250 may be formed so that the wires can be divided and connected on both sides of the head gear 100.

The neck brace 230 may be joined to the wire separator 250 through a protruding joint 251. Through this, it is possible to support the wire separator 250 and the wire behind the user's neck. Through this, as the wire of the assistive wearable system 10 comes into contact with the user's body, it is possible to prevent the tension load on the wire controller from increasing due to shortening of the distance from the user's cervical spine to the wire (i.e. moment arm of torque generated by wire tension), or it is possible to prevent the tension load on the wire controller from increasing due to friction resulting from contact between the wire and the user's body. Additionally, skin damage or wire damage that may occur when the wire touches the user's body can be prevented.

The wire separator 250 is formed in combination with the neck brace 230, so that the operation of the assistive wearable system 10 can be facilitated by more sensitively detecting the user's behavior (e.g. nodding his or her head back and forth) to use the assistive wearable system 10. In addition, the wire separator 250 divides the wire connecting the head gear 100 and the wire tension controller 300 in the direction of both sides of the head gear 100, so that when tension of the wire occurs, tension is applied to the back of the user's head compared to when the wire is connected to the back of the head, and it is possible to prevent the head gear 100 from peeling off. In addition, the head gear 10 is connected to the wire separator 250 through a wire on both sides, the wire separator 250 does not protrude significantly from the back of the head, so that the assistive wearable system 10 can not only achieve a space-efficient and aesthetic effect, but the wire is fixed at a position close to the center of the user's head, making it easy to control the head posture even while using the assistive wearable system 10. In addition, by separating and connecting wires to both sides of the head gear 100 through the wire separator 250, the user's convenience in the work environment can be improved by providing mobility so that the user can move his or her head left and right while fixing his or her head using the assistive wearable system 10.

The wire tension controller 300 is formed by being seated on the rear of the wearable platform 200 and may be connected to the head gear 100 with a wire. The wire tension controller 300 can maintains the tension of the wire by fixing a semi-active ratchet mechanism that acts as a brake to detect a moment a movement of the wire stops, and stop unwinding of the wire. At this time, the moment the movement of the wire stops may be a signal for the user to operate the assistive wearable system 10. In other words, it becomes possible to semi-automatically operate the assistive wearable system 10 through simple actions (for example, the user nods his or her head back and forth and then stops his or her head at a specific angle to stop the unwinding of the wire through an incremental encoder in the wire tension controller 300, which will be described later), so that the user is free from any actions (action using the user's hands) to operate the assistive wearable system 10. For example, while the user uses the assistive wearable system 10, a situation may arise in which the user must maintain a different head angle depending on the work situation and work progress in an environment where the user works with both hands. At this time, the user can operate the assistive wearable system 10 simply by nodding his or her head, and it can be expected to improve the user's convenience by ensuring the autonomy of other body parts, including the user's both hands.

The wire tension controller 300 may include an incremental encoder that detects an amount of rotation of a wire winding frame in the wire tension controller according to the movement of the wire, a pawl for fixing a ratchet in the wire tension controller and a rotation of the ratchet to maintain the tension of the wire, a ball plunger for holding the pawl in different locations according to the fixation and release of the pawl based on rotation of the ratchet, and a power unit that operates the pawl based on an electrical signal from the incremental encoder based on the movement of the wire. Additionally, the wire tension controller 300 may include a separate battery to operate the power unit, and may include a separate control board to operate the wire tension controller 300 at a preconfigured value.

The incremental encoder may generate the electrical signal that operates to cause the pawl to fix the rotation of the ratchet when the amount of rotation of the wire winding frame connected to the wire is not detected due to no movement of the wire for a predetermined period of time. At this time, the predetermined time may be 3 seconds. In addition, the case where the movement of the wire disappears may be based on the user's action to operate the assistive wearable system 10 (for example, the user nods his or her head back and forth).

The pawl can prevent rotation of the ratchet by engaging the ratchet to stop unwinding of the wire due to rotation of the ratchet in the wire tension controller 300. Additionally, the pawl may be formed with a locking protrusion. The locking protrusion may be formed to protrude.

The ball plunger may be composed of a ball that is elastically pressed by a spring. The shape of the ball plunger may prevent the pawl and the locking protrusion formed with the pawl from rotating due to the rotation of the ratchet, and thus maintain the pawl in different positions so that the pawl is supported at a certain angle through the elastic force transmitted by the ball plunger. Afterwards, when a force sufficient to overcome the elastic force (for example, the user nodding his or her head back and forth) is applied, as the ball plunger pushes out the ball, the pawl and locking protrusion may rotate in the opposite direction of their current state. The power unit may detect the electrical signal generated from the incremental encoder and generate power to operate the pawl. At this time, the power unit may be a solenoid motor. In addition, the power unit does not continuously consume power to maintain the tension of the wire, but only consumes power when operating the pawl to prevent rotation of the ratchet in the wire tension controller 300 when no movement of the wire is detected. In other words, in a work environment that requires working in a fixed position for a long period of time, a user using the assistive wearable system 10 can continue working without being affected by time.

Figure 2A:
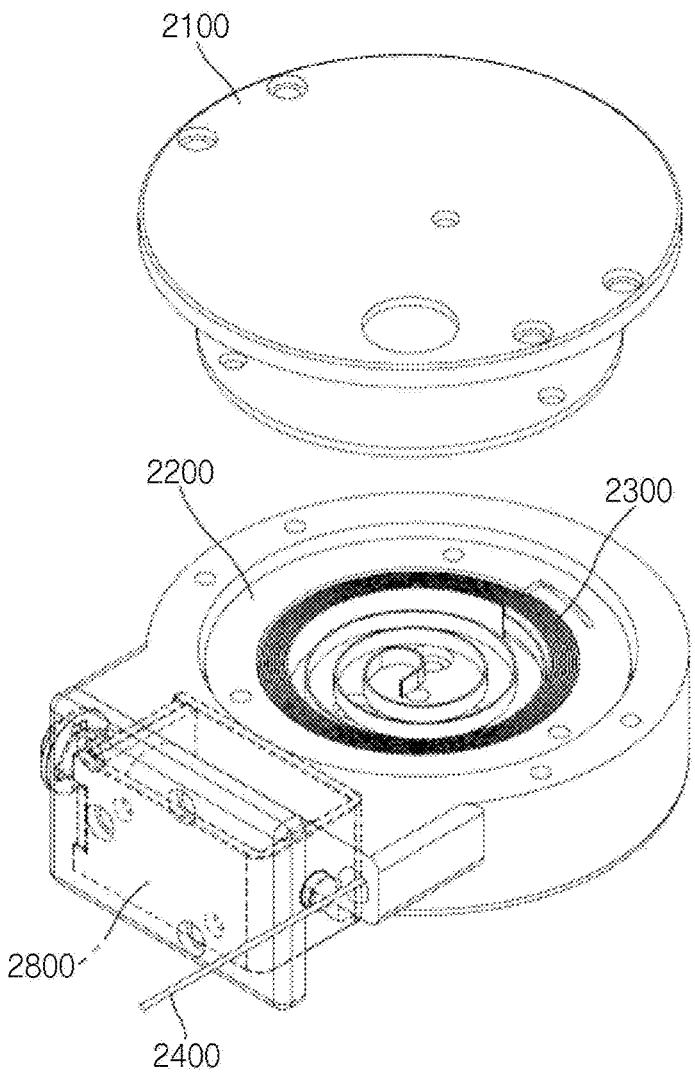
FIGS. 2A to 2C are diagrams for explaining a semi-active ratchet mechanism according to an embodiment of the present disclosure.
Figure 2B:
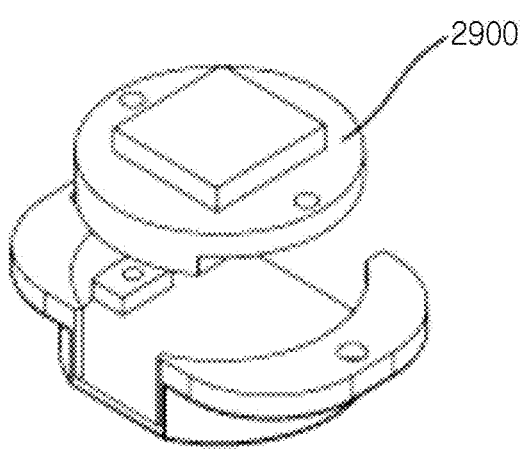
Figure 2C:
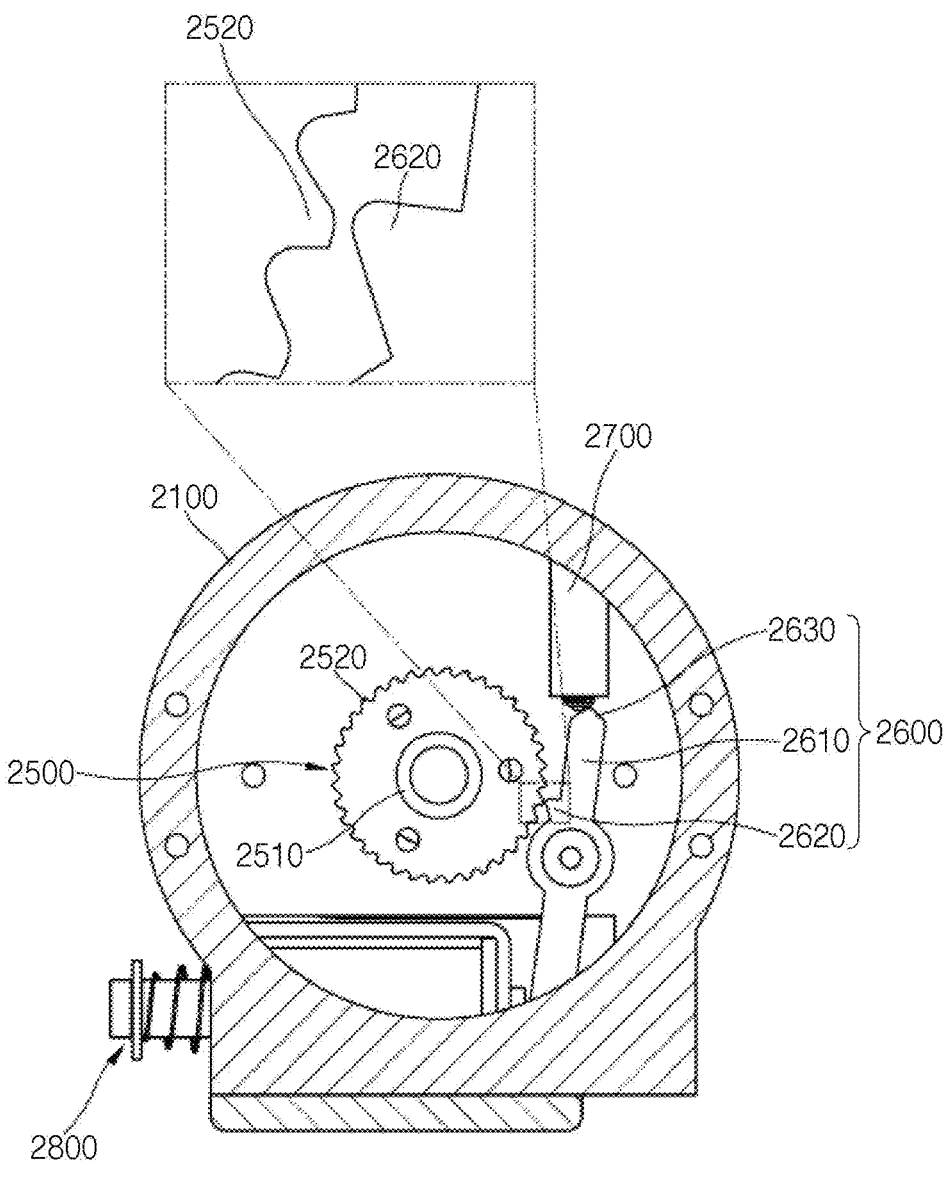

A detailed description of the wire tension controller 300 will be supplemented through the description of FIGS. 2A to 2C. Additionally, the wire tension controller 300 is not limited to the description of FIGS. 2A to 2C, and may also be implemented through an apparatus using another semi-active ratchet mechanism.

FIGS. 2A to 2C are diagrams for explaining a semi-active ratchet mechanism according to an embodiment of the present disclosure.

Referring to FIGS. 2A to 2C, a ratchet gear apparatus (e.g. a wire tension controller 300 in FIG. 1A) may include a base 2100, a winding frame 2200 (e.g. a wire winding frame in the wire tension controller 300 of FIG. 1A), a winding spring 2300, a wire 2400 (e.g. a wire in FIG. 1A), a ratchet 2500, a locking member 2600, and a locking maintaining member 2700.

The base 2100 corresponds to the main body of the ratchet gear apparatus according to one embodiment, and may be configured so that other components mentioned above can be installed and fixed. In some cases, an empty space may be provided inside so that the above configurations can be accommodated and installed.

The winding frame 2200 may be formed in a cylindrical shape and rotatably installed on the base 2100. The winding frame 2200 is preferably installed so that it can rotate smoothly with respect to the base 2100 through a bearing-like configuration. In one embodiment, the ratchet 2500 may be installed on the base 2100 through a bearing, and the winding frame 2200 is coupled to the ratchet 2500, so that the winding frame 2200 can be rotatable with respect to the base 2100.

The winding spring 2300 may be disposed inside the winding frame 2200. One end of the winding spring 2300 may be coupled to a rotating shaft installed on the base 2100, and the other end may be coupled to the inner periphery of the winding frame 2200. The winding spring 2300 may be arranged to be wound or unwound within the winding frame 2200. The winding spring 2300 may provide an elastic force to the winding frame 2200 in a direction to rotate the winding frame 2200 so that the wire 2400 is wound around the winding frame 2200.

The wire 2400 may be installed with its end fixed to the winding frame 2200 and wound around the winding frame 2200. The opposite end of wire 2400 may be connected to an external apparatus or component. When the tension applied to the wire 2400 increases, the wire 2400 may be released from the winding frame 2200, and when the tension applied to the wire 2400 decreases, the wire 2400 may be wound around the winding frame 2200 by the action of the winding spring 2300.

The ratchet 2500 may be arranged coaxially with the winding frame 2200 and may be installed to be rotatable with respect to the base 2100 together with the winding frame 2200. The ratchet 2500 can be easily rotated about the rotation axis of base 2100 by being connected to the base 2100 through the bearing 2510. A plurality of teeth 2520 (e.g. teeth within the wire tension controller 300 of FIG. 1A) may be formed on an outer circumference of the ratchet 2500 along the circumferential direction.

The locking member 2600 may be configured to act on the ratchet 2500 to prevent or allow rotation of the ratchet 2500. The locking member 2600 may include a locking body 2610, a pawl 2620 (e.g. a pawl in wire tension controller 300 of FIG. 1A), and a locking protrusion 2630. The locking member 2600 may be rotatably installed with respect to the base 2100. According to one embodiment, the locking member 2600 may be installed on the base 2100 so as to be rotatable about a rotation axis disposed in parallel and spaced a predetermined distance from the rotation axis of the ratchet 2500. The locking body 2610 may be formed in the shape of a long bar extending in the longitudinal direction. The pawl 2620 and the locking protrusion 2630 may each be formed to protrude with respect to the locking body 2610. The pawl 2620 may be formed to protrude from the side of the locking body 2610, and the locking protrusion 2630 may be formed to protrude from the end of the locking body 2610.

When the pawl 2620 of the locking member 2600 rotates in a direction approaching the ratchet 2500 and the pawl 2620 is caught on the teeth 2520 of the ratchet 2500 rotation of the ratchet 2500 in the direction (hereinafter, clockwise) in which the wire 2400 is unwound from the winding frame 2200 may be prevented. Accordingly, even if tension is applied to the wire 2400 and the wire 2400 is pulled, the ratchet 2500 may not rotate because the ratchet 2500 is locked by the pawl 2620. To this end, the teeth 2520 of the ratchet 2500 and the pawl 2620 of the locking member 2600 may be formed with a protruding slope so as to engage each other with respect to clockwise rotation of the ratchet 2500.

When the tension on the wire 2400 is reduced or removed, the ratchet 2500 may rotate in the direction in which the wire 2400 is wound around the winding frame 2200 by the elastic force of the winding spring 2300. In one embodiment, the ratchet 2500 may rotate in a counterclockwise direction. When the winding frame 2200 rotates in the direction in which the wire 2400 is wound, locking member 2600 may rotate in a direction such that the pawl 2620 is away from ratchet 2500 as the pawl 2620 is pushed by the teeth 2520 due to the shape of the teeth 2520 of the ratchet 2500 and the pawl 2620. Accordingly, the locking state of the ratchet 2500 by the pawl member 2600 may be released. The wire 2400 may be wound around the winding frame 2200 until the elastic force of the winding spring 2300 is exhausted, or the wire 2400 may be wound around the winding frame 2200 until tension is applied to the wire 2400 again.

The locking maintaining member 2700 may maintain the angular displacement of the locking member 2600 at an angle at which the locking member 2600 locks the ratchet 2500 and an angle at which the locking member 2600 unlock the ratchet 2500, respectively. That is, the locking maintaining member 2700 can maintain the angle of the locking member 2600 at a locking angle at which the pawl 2620 of the locking member 2600 is caught on the teeth 2520 of the ratchet 2500, or can maintain the angle of the locking member 2600 at an unlocking angle at which the pawl 2620 of the locking member 2600 is not caught on the teeth 2520 of the ratchet 2500.

In one embodiment, a ball plunger consisting of a spring and a ball elastically pressed by the spring may be used as the locking maintaining member 2700. The locking maintaining member 2700 in the form of a ball plunger may be disposed at a position where it is caught on the locking protrusion 2630 of the locking member 2600 when the locking member 2600 rotates at the locking angle and the unlocking angle, respectively. Accordingly, the locking maintaining member 2700 can maintain the locking member 2600 at the locking angle and the unlocking angle by the elastic force transmitted by the ball plunger, respectively. When a force sufficient to overcome the elastic force of the locking maintaining member 2700 is applied to the locking member 2600, as the locking protrusion 2630 of the locking member 2600 pushes out the ball of the ball plunger, the locking member 2600 can rotate in the opposite direction of its current state and move to a position that is the unlocking angle or locking angle, respectively.

Referring to FIG. 2B, a pawl operating member 2800 (e.g. a power unit in the wire tension controller 300 of FIG. 1A) may be installed on the base 2100. The pawl operating member 2800 may rotate the locking member 2600 at a locking angle at which the pawl 2620 of the locking member 2600 is caught on the teeth 2520 of the ratchet 2500. The pawl operating member 2800 may be used of various configurations capable of rotating the pawl member 2600 with a locking angle by applying an external force to the pawl member 2600 including manually operated push-pull button. In one embodiment, the case of using the pawl operating member 2800 composed of a solenoid motor and a permanent magnet will be described as an example.

When the pawl operating member 2800 operates according to an electrical signal generated by a controller separately provided in the ratchet gear apparatus, the pawl operating member 2800 may push the locking member 2600 to rotate the locking member 2600 to a locking angle. Due to the operation of the controller and the pawl operating member 2800, the ratchet 2500 may be caught in the pawl 2620, so that the rotation of the ratchet 2500 is locked and the wire 2400 can no longer be released.

The generation of an electrical signal that causes the controller to operate the pawl operating member 2800 may be manually input by a user's command, but may be configured so that the controller operates according to the measured value of a winding frame sensor 2900 (e.g. the incremental encoder in wire tension controller 300 of FIG. 1A)

The winding frame sensor 2900 may be installed on the base 2100 to measure the angular displacement of the winding frame 2200. The angular displacement of the winding frame 2200 measured by the winding frame sensor 2900 may be transmitted to the controller. The controller may operate the pawl operating member 2800 when the winding frame 2200 rotates more than a predetermined angle based on the measured value of the winding frame sensor 2900. In some cases, if the angular displacement of the winding frame 2200 does not change for more than a predetermined time, the pawl operating member 2800 may be operated to operate the locking member 2600 to fix the wire 2400.

Hereinafter, the operation of the ratchet gear apparatus configured as described above will be described.

When the locking member 2600 is at the unlocked angle, the pawl 2620 does not interfere with or contact the ratchet 2500, so the winding frame 2200 can be freely rotated.

When tension is applied to the wire 2400, the wire 2400 is released from the winding frame 2200 and the ratchet 2500 can rotate clockwise.

At this time, since the locking protrusion 2630 is caught on the ball plunger-shaped locking maintaining member 2700, the locking member 2600 can be maintained at the unlocking angle. Unless a force sufficient to overcome the elastic force of the locking member 2700 acts on the locking member 2600, the locking member 2600 can maintain the state of the unlocking angle by the locking maintaining member 2700.

In this state, when the external force acting on the wire 2400 is reduced or removed, as the winding frame 2200 rotates counterclockwise due to the action of the winding spring 2300, the wire 2400 can be wound around the winding frame 2200.

Conversely, when a force sufficient to overcome the elastic force of the winding spring 2300 acts on the wire 2400, the wire 2400 can be freely released from the winding frame 2200.

In this state, when the controller generates a control signal to the pawl operating member 2800, as the pawl operating member 2800, which may be a solenoid motor, is extended, the locking member 2600 can be pushed out and the locking member 2600 can be rotated at the locking angle. As the locking protrusion 2630 of the locking member 2600 pushes the ball plunger-shaped locking maintaining member 2700 by the pawl operating member 2800, the locking member 2600 can rotate counterclockwise. Accordingly, the pawl 2620 of the locking member 2600 is caught on the teeth 2520 of the ratchet 2500, thereby preventing clockwise rotation of the ratchet 2500.

As described above, when the condition such that the angular displacement of the winding frame 2200 measured by the winding frame sensor 2900 is maintained in a constant state for more than a predetermined time is satisfied, the controller may operate the pawl operating member 2800. Accordingly, even if the ratchet 2500 is locked and the tension pulling the wire 2400 increases, the winding frame 2200 may not rotate.

This ratchet gear apparatus can be used in various fields. In particular, when used in a wearable robot, it can be used to help the user maintain a specific posture for a long time. For example, it can be used to help doctors maintain a head-down position for a long time during surgery or to help factory workers maintain a posture with their arms raised for long time, and can be used to prevent fatigue and injury in specific parts of the user. In other words, if the operating doctor maintains a head-down angle for more than 3 seconds, the controller operates the pawl operating member 2800 to fix the ratchet 2500 so that the wire 2400 connected to the doctor's head is no longer released from the winding frame 2200.

In this state, when the doctor performs an operation to reduce or remove tension on the wire 2400, such as lifting the head, as the wire 2400 is wound around the winding frame 2200 by the action of the winding spring 2300, the winding frame 2200 can rotate counterclockwise. As described above, the pawl 2620 of the locking member 2600 may be arranged only at an angle that can prevent the ratchet 2500 from rotating clockwise due to the shape of the teeth 2520 of the ratchet 2500. Therefore, when the ratchet 2500 rotates counterclockwise, the fixation by the pawl 2620 is released and the locking member 2600 is pushed by the ratchet 2500 so that it can rotate at the unlocking angle. When the teeth 2520 of the ratchet 2500 push out the locking member 2600 by the force transmitted by the elastic force of the winding spring 2300, the locking protrusion 2630 overcomes the elastic force of the locking maintaining member 2700 and rotate at the unlocking angle.

In this state, the wire 2400 freely moves forward or backward due to external force and the elastic force of the winding spring 2300, and can be freely wound or unwound from the winding frame 2200.

Since the locking maintaining member 2700 maintains the locking member 2600 at the unlocking angle by its own elastic force, the locking member 2600 may not affect the movement of the ratchet 2500 until the pawl operating member 2800 operates again In this way, the ratchet gear apparatus has the advantage of being able to automatically unlock the winding frame 2200 simply by actively locking the clockwise rotation of the winding frame 2200 by the pawl operating member 2800, and simply by rotating the winding frame 2200 in the opposite direction without using any other operating members to release the lock. Using these operating characteristics, it is possible to effectively use it in various technological fields, including wearable robots.

In addition, the ratchet gear apparatus has the advantage of being able to easily adjust the combination of locking and unlocking operations as needed by variously adjusting the operating conditions of the locking member 2600 by operating the controller.

Additionally, the racket gear apparatus has the advantage of being able to miniaturize the configuration of the ratchet gear apparatus that performs the locking operation since it is easy to configure the space in which the locking member 2600 rotates between the locking angle and the unlocking angle to be small. Through this, it can be utilized by being attached to a wearable platform that a user can wear (e.g. the wearable platform 200 of FIG. 1A).

Additionally, the racket gear apparatus has the advantage of enabling an immediate and accurate unlocking operation without backlash since the racket gear apparatus can change the locking member 2600 to the unlocking angle simply by pushing the teeth 2520 of the ratchet 2500 against the pawl 2620 for the locking operation.

Although the ratchet gear apparatus has been described as a preferred example, the scope of the ratchet gear apparatus is not limited to the form described and shown above.

According to the above-described embodiments of the present disclosure, by proposing a assistive wearable system capable of maintaining the user's head-down posture, it was confirmed that muscle fatigue of the Splenius Capitis and Trapezius muscles was reduced. As an experimental sample, 22 adult men and women aged 20 to 64 years (average age 24.7 years, average BMI 20.1 $kg/m^2$) were randomly selected. The effect of relieving muscle fatigue was analyzed by measuring the average power frequency of surface electromyography in a position with test subjects' heads bent at 45 degrees for 15 minutes, depending on whether or not they were wearing the assistive wearable system 10 of FIG. 1A. As a result, when the user wears the assistive wearable system 10 compared to when the user does not wear the assistive wearable system 10, it showed an effect of improving fatigue by 7.83% in the splenius capitis muscle and 13.81% in the trapezius muscle. In addition, it is possible to provide an wearable system that is robust in terms of power consumption by assisting the user at the user's desired head angle by minimizing the power consumption of the wearable system for maintaining the bowed posture.

Most of the terms used in the present disclosure are selected from common ones widely used in the field, but some terms are arbitrarily selected by the applicant and their meanings are described in detail in the following description as necessary. Accordingly, the present disclosure should be understood based on the intended meaning of the terms and not the mere names or meanings of the terms.

It is obvious to those skilled in the art that the present disclosure can be embodied in other specific forms without departing from the essential features of the present disclosure. Accordingly, the above detailed description should not be construed as restrictive in all respects and should be considered illustrative. The scope of the present disclosure should be determined by reasonable interpretation of the appended claims, and all changes within the equivalent scope of the present disclosure are included in the scope of the present disclosure.

What is claimed is:

1. An assistive wearable system comprising:
a head gear mounted to cover a head of a user;
a wearable platform configured to be mounted on an upper body of the user; and
a wire tension controller seated on the wearable platform and connected to the head gear by a wire to detect a moment when a movement of the wire stops and to operate a semi-active ratchet mechanism structure as a brake to stop unwinding of the wire,
wherein the semi-active ratchet mechanism structure rotates a ratchet based on the unwinding and pulling of the wire,
wherein the wearable platform further includes:
a wire separator that divides and connects the wire to both sides of the head gear; and
a neck brace that is joined to the wire separator through a protruding joint and is attached to an upper part of the wearable platform to support the wire separator and the wire configured to be behind a neck of the user and is configured to be coupled to the upper body of the user.

2. The assistive wearable system of claim 1, wherein the wearable platform includes a wire sheath located at a rear of the wearable platform and spaced apart from the wire tension controller to prevent rotational torque caused by twisting or lifting left and right according to a movement of the user and to maintain the tension of the wire.

3. The assistive wearable system of claim 1, wherein the wire tension controller, connected to the head gear by the wire, includes:
an incremental encoder that detects an amount of rotation of a wire winding frame in the wire tension controller according to the movement of the wire;
a pawl for fixing the ratchet in the wire tension controller and a rotation of the ratchet to maintain the tension of the wire;
a ball plunger for holding the pawl in different locations according to the fixation and release of the pawl based on rotation of the ratchet; and
a power unit that operates the pawl based on an electrical signal from the incremental encoder based on the movement of the wire.

4. The assistive wearable system of claim 3, wherein the incremental encoder generates the electrical signal that operates to cause the pawl to fix the rotation of the ratchet when the amount of rotation of the wire winding frame connected to the wire is not detected due to no movement of the wire for a predetermined period of time.

5. The assistive wearable system of claim 3, wherein the pawl prevents rotation of the ratchet by engaging the ratchet to stop unwinding of the wire due to rotation of the ratchet.

6. The assistive wearable system of claim 3, wherein the power unit detects the electrical signal generated from the incremental encoder and provides power to operate the pawl.

7. The assistive wearable system of claim 1, wherein the head gear, connected to the wire tension controller by the wire, further includes:
an inertial measurement unit (IMU) sensor capable of measuring head angle information of the user using tilt inertia according to the head angle of the user.

* * * * *